United States Patent [19]

Koester

[11] 4,410,245
[45] Oct. 18, 1983

[54] IMAGE STABILIZATION METHOD, AND APPARATUS

[76] Inventor: Charles J. Koester, 60 Kent Rd., Glen Rock, N.J. 07452

[21] Appl. No.: 139,669

[22] Filed: Apr. 14, 1980

Related U.S. Application Data

[60] Continuation-in-part of Ser. No. 42,085, May 24, 1979, Pat. No. 4,241,257, which is a division of Ser. No. 902,277, May 3, 1978, Pat. No. 4,170,398.

[51] Int. Cl.$^3$ .............................................. A61B 3/10
[52] U.S. Cl. .................................. 351/219; 351/205; 350/500
[58] Field of Search ................... 351/6, 7, 16; 354/62; 350/500

[56] References Cited

FOREIGN PATENT DOCUMENTS 148200 10/1960 U.S.S.R. .................................. 351/6

OTHER PUBLICATIONS

Koenderink et al., Method of Stabilzing the Retinal Image Applied Optics, vol. 13 No. 4, Apr. 1974.
Koenderink, Contrast Enhancement and the Negative After Image JJ Koenderink, Journal of the Optical Society of America, vol. 62, No. 5, May. 1972.
A. L. Yarbus, *Eye Movement and Vision* (Plenum, N.Y.: 1967), pp. 35-38 and 142-143.
Riggs et al., "The Disappearance of Steadily Fixated Visual Test Objects," *Journal of the Optical Society of America*, vol. 43, No. 6, (Jun., 1953), pp. 495-501.
Ratliff, "The Role of Physiological Nustagmus in Monocular Acuity" *Journal of Experimental Psychology*, vol. 43, No. 3 (Mar., 1952), pp. 163-172.
Ditchburn et al., "Vision With A Stabilized Retinal Image", *Nature*, vol. 170 (Jul. 5, 1952), pp. 36-37.

*Primary Examiner*—John K. Corbin
*Assistant Examiner*—Rodney B. Bovernick
*Attorney, Agent, or Firm*—Sandler & Greenblum

[57] ABSTRACT

A method of reducing the effects of rotational motion and jitter of an object comprising forming a virtual image of the region or plane being examined at the center of rotation of the object by means of a lens or mirror fixed with respect to the object and viewing the virtual image of the region or plane. An optical system for viewing a region or plane of an object adapted to reduce the effects of rotational motion and jitter of the object by providing a virtual image of the region or plane at the center of rotation of the object. Image stabilization apparatus comprising an optical instrument for viewing a plane or region of an object and means rigidly affixed to the object for forming a virtual image of the plane or region substantially at the center of rotation of the object as the plane or region is viewed through the optical instrument. Image stabilization apparatus comprising an optical instrument adapted to project an image to the center of rotation of the eye of an observer and a contact lens affixed to the eye of the observer adapted to form the image from the instrument on the retina of the eye.

31 Claims, 12 Drawing Figures

IMAGE STABILIZATION METHOD, AND APPARATUS

CONTINUING DATA

This application is a continuation-in-part of application Ser. No. 42,085 filed May 24, 1979 now U.S. Pat. No. 4,241,257 which is a divisional application of application Ser. No. 902,277 filed May 3, 1978, now U.S. Pat. No. 4,170,398 the disclosures of which are hereby completely incorporated by reference.

BACKGROUND OF THE INVENTION

1. Field of the Invention

The invention relates to an image stabilization system for diagnostic eye examination.

2. Description of Prior Art

In a number of diagnostic procedures it is necessary to examine detail within the eye using optical instruments such as ophthalmoscopes, biomicroscopes, or specular microscopes. The patient's eye, however, is never actually stationary for a period of time long enough to perform a detailed examination. For low magnification applications, such as the indirect ophthalmoscope, eye motion is of little consequence. However, when using instruments having higher magnification, eye motion becomes increasingly troublesome as the magnification is increased. An example is the visualization of the endothelial cells of the cornea.

Voluntary eye motions can be controlled by a cooperative patient. However, there are frequent motions which are involuntary and are not controllable by even the most cooperative subject. These small, sudden motions or microsaccades occur on the order of 70 times per minute. The tremors may extend over only 5 or 6 minutes of an arc; which in fact corresponds to one or more endothelial cell diameters. Furthermore, any changes in the longitudinal position of the cornea results in defocus of the image.

If, for example, the eye makes a sudden rotational movement of half a degree, the cornea will move laterally approximately 0.1 mm. Endothelial cells are approximately 0.025 mm in width, therefore the motion of the cornea in this example would be equivalent to four cell widths. In a microscope system designed to view the cells at high magnification, such motion of the image makes detailed study of the cells difficult if not impossible. Present methods involve photography of the image using a flash lamp to stop the motion. While this technique produces satisfactory photographic results, it is often desirable to examine the endothelial cells visually in detail. A method for stabilizing the image is therefore highly desirable.

One previously used technique for decreasing the motion of the eye during a procedure known as specular microscopy has been to contact the cornea with a so-called dipping cone objective. In this technique the outer-most element of the objective has a flat, polished glass surface. When the objective is in contact with the cornea, rotational motion of the eye is inhibited (but not entirely eliminated).

The major disadvantage of this technique is that any motions of the eye relative to the dipping cone can cause epithelial cells to be abraded off of the cornea. While the cornea is anesthetized, the pressure against the eye is felt by the patient and is uncomfortable. Continued use of the dipping cone for thorough studies of the cornea can lead to a roughened epithelial surface. And while the body repairs this tissue in a matter of hours, the degraded optical quality of the exterior surface of the cornea decreases the quality of the images which can be obtained.

Diagnostic contact lenses are known in the art. Such lenses generally are hand-held in contact with the cornea, and as a result, do not move with the eye as it rotates. Their primary function is to permit the fundus of the eye and certain other interior regions of the eye to be viewed at low magnification, for example, through a biomicroscope. Such lenses do not reduce the effect of eye rotation on the image to any substantial extent.

SUMMARY OF THE INVENTION

It is, therefore, an object of the invention to provide method and apparatus for stabilizing images which might normally be subject to blurring due to rotational movements of the specimen.

This and other objects ae fulfilled by means of the method of the invention for reducing the effects of rotation and jitter of an object while examining a region or plane within or on the object. The method comprises forming a virtual image of the region or plane of interest at the center of rotation of the object by means of a lens or mirror which moves with the object and viewing the virtual image of the region or plane.

Although broadly applicable to many situations in which a rotating object is to be viewed or examined, the method of the invention finds particular application when examining certain regions or portions of the eye which is itself normally subject to a certain amount of involuntary rotational jitter on the part of the patient.

The invention is further directed to an optical system for viewing a region or plane within or on an object. The contact lens is adapted to reduce the effects of rotational motion and jitter of the object on the image being viewed. The contact lens is adapted to provide a virtual image of the region or plane at the center of rotation of the object.

Various contact lens configurations are possible within the scope of the invention provided that they serve to form at the center of rotation of the object a virtual image of the region or plane viewed through the lens.

The apparatus and method may be used to view the endothelial cell layer, the cornea, the eye lens, the vitreous, the retina, or the angle of the interior chamber, for example.

The invention is further directed to an image stabilization apparatus which comprises an optical instrument for viewing a region or plane on or in an object which rotates or jitters around a center of rotation and means for forming a virtual image of the plane or region substantially at the center of rotation of the object so as to minimize the effects of jitter and rotation as the plane or region is viewed through the instrument.

In addition to being able to use a wide variety of different types of contact lenses, the apparatus of the invention may be equally used with a wide variety of optical instruments.

The invention also finds application in an image stabilizing apparatus in which it is desired to form a stabilized image on the observer's retina. Thus an optical instrument is adapted to form a virtual image at the center of rotation of the observer's eye, a contact lens is affixed to the eye, the contact lens being adapted to form a real image on the observer's retina.

DESCRIPTION OF PREFERRED EMBODIMENTS

The contact lens of the invention is adapted to move with the eye during its small, frequent rotations and is designed to form a virtual image of the plane or region of interest at the center of rotation of the eye. Because the virtual image is located at the center of rotation of the eye, the image does not translate laterally or longitudinally as the eye rotates, as long as the contact lens moves with the eye. This virtual image is then reimaged by a stationary optical system for visual examination or photography. The plane of interest may be the endothelial or epithelial cell layers of the cornea, the epithelial cell layer of the lens, or regions within the depth of the lens or the vitreous region or the retina. The optical power of the contact lens, along with its thickness, determines the depth within the eye of the region or plane which is imaged at the center of rotation.

Figure 1:
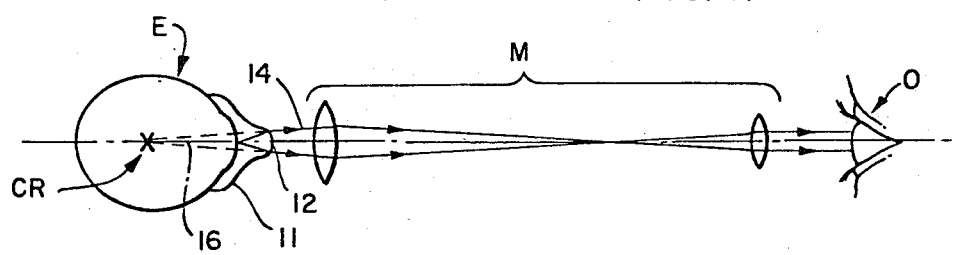
FIG. 1 is a schematic view of the inventive device.

FIG. 1 illustrates a simple embodiment of the invention. As may be seen from the Figure, contact lens 11 is of the scleral type, in that the lens fits over the entire cornea and onto a portion of the sclera. The central portion 12 of the contact lens is several millimeters in thickness and has a strong convex surface. For examination of the endothelium, the focal length of this lens is selected such that the virtual image of the endothelium is formed at the center of rotation of the eye. Actual rays from the endothelium are shown as solid lines 14. Dashed lines 16 illustrate the apparent path of rays, as seen from the right side of surface 12. They appear to originate at the virtual image, located at CR. The microscope M, is stationary and is focused on this virtual image. In one preferred embodiment a scanning microscope apparatus of the type disclosed in U.S. Pat. No. 4,170,398, the disclosure of which is hereby incorporated by reference, may be used. Thus, the observer sees an essentially stationary image even when the eye E undergoes small rotational movements.

Figure 2:
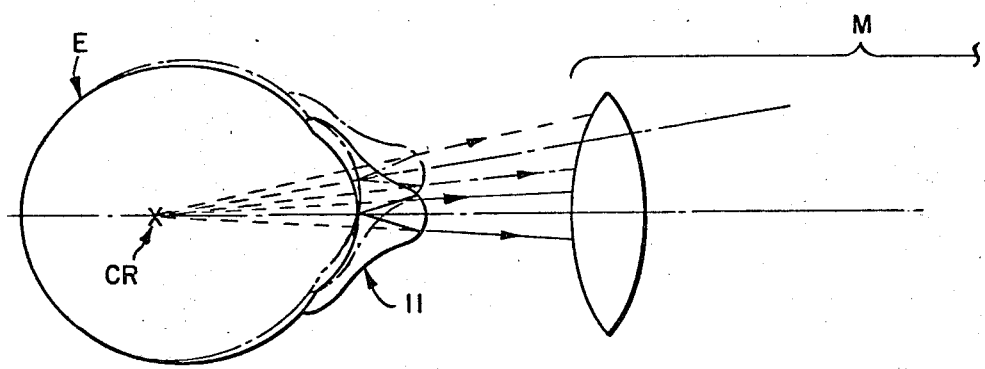
FIG. 2 illustrates the operation of the device as the eye rotates.

Turning to FIG. 2, the path of rays is illustrated for two different positions of the eye. While the directions of the rays leaving the contact lens are different in the two cases, in each case, the rays appear to be coming from the same point in space, i.e., the center of rotation. Therefore, to an observer at the right of the microscope M, the image will appear to be stationary except for a small rotation of the image. It may also be seen from FIG. 2 that if the eye rotates beyond the point at which the rays leaving the contact lens 11 can enter the aperture of the observation system, the image will no longer be seen. For regions of interest deeper within the eye the contact lens should have a less positive power as will be seen below.

Figure 3:
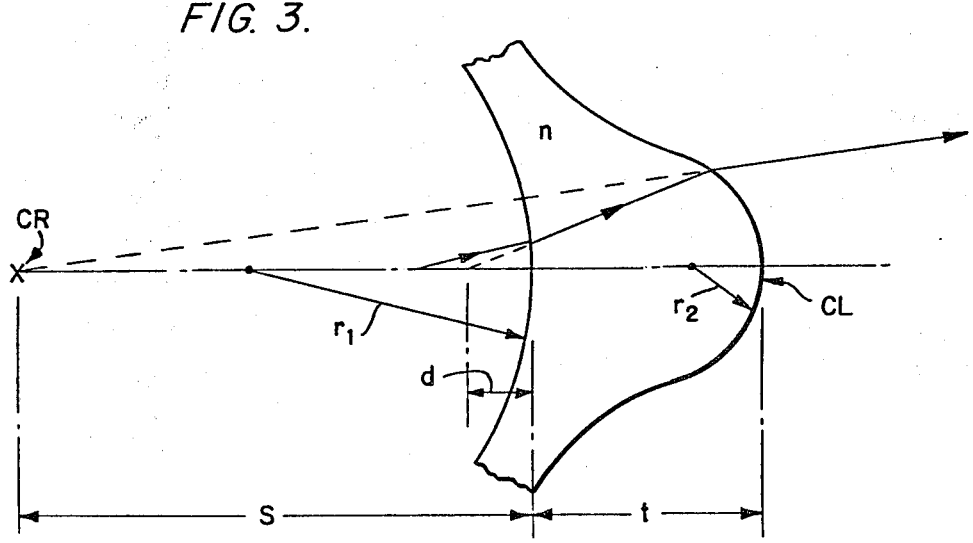
FIG. 3 illustrates the parameters used for calculating the various lens parameters.

Calculation of the power of the contact lens and its thickness involves the depth of the region of interest and the location of the center of rotation. With reference to FIG. 3, the vergence equation for the contact lens/air interface is $$-\frac{n}{d+t} + \frac{n-1}{r_2} = -\frac{1}{t+s} \quad (1)$$

where:

n = index of refraction of the contact lens t = thickness of the contact lens $r_2$ = radius of curvature of the anterior surface of the contact lens (a positive quantity)

s = distance from the cornea apex to the center of rotation of the eye (a positive quantity). For the adult population, the average value of s is 13.5 mm.

d = apparent depth of the plane of interest as seen from the medium of the contact lens and measured from the apex of the cornea (d is also positive). The distance d can be expressed in terms of the vergence $V_1$ of the light from the plane of interest as this light is incident on the cornea/contact lens interface. The vergence equation at this interface is $$V_1 = \frac{1.376 - n}{r_1} = -\frac{n}{d} \quad (2)$$

where:

$r_1$ = the radius of the posterior surface of the contact lens. It is assumed that the cornea assumes the same radius.

1.376 = index of refraction of the cornea Solving equation (1) for $r_2$, and eliminating d by means of equation 2 yields $$r_2 = \frac{(n-1)(s+t)[t(r_1V_1 - n + 1.376) - nr_1]}{[ns + t(n-1)](r_1V_1 - n + 1.376) + nr_1} \quad (3)$$

For example, we take the thickness of the cornea to be 0.5 mm (0.0005 m). At the left of the cornea/contact lens interface the vergence $V_1$ of light emanating from a point on the endothelial surface is given by $$V_1 = -\frac{1.376}{.0005} = -2752 \text{ Diopters.}$$

In this example we also take n = 1.49, t = 5 mm (0.005 m), s = 0.0135 m, $r_1$ = 0.0078 m. From equation (3) we obtain $r_2$ = 0.00228, or 2.28 mm.

Figure 4:
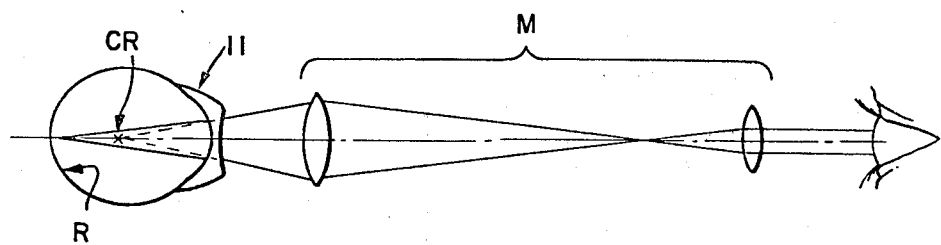
FIG. 4 is a schematic view of the device using a contact lens adapted to view the retina.

FIG. 4 illustrates an arrangement for examining and stabilizing an image of the subject's retina R. As was previously the case, the contact lens 11 is mounted so as to extend to the sclera. Since the retina, R, is located behind the center of rotation, CR, a negative power will be required in the contact lens, 11, so as to bring the virtual image forward to the center of rotation. The observing microscope, M, is focused on this virtual image at the center of rotation.

The calculation of the required lens curvature is similar to that above, except that the vergence $V_1$ can be determined by a different approach. An emmotropic eye, i.e., without refractive error, focuses light from a distant object on the retina. The average cornea has a power of 43 diopters. If the emmotropic eye is considered in reverse, with light coming from the retina towards the cornea, it must be true that as the light is incident on the cornea-air interface, it will have a vergence of $-43$ diopters. Therefore, for the emmetropic eye $V_1 = -43$ D.

When this value is substituted in equation 3, together with a thickness $t = 0.001$ m, $r_1 = 0.0078$ m, and $n = 1.49$, the radius $r_2$ is found to be $r_2 = -0.0363$ m or $-36.3$ mm. the minus sign indicating that the lens is to have a concave surface.

For a patient who is not emmotropic, that is who has a non-negligible refractive error, the power of the contact lens must be adjusted as indicated below.

Quite obviously, visualization and stabilization of planes at other depths within the eye will require contact lenses having powers different from those calculated above.

In general, a lens with a power which is approximately equal to the value derived by the above equation will form a virtual image of the region or plane of interest close to the center of rotation, and even though it is not exactly at the center of rotation the apparent motion of that plane will be substantially reduced. Due to anatomical variations, it is possible that for a particular eye the power of a given contact lens will not be exactly correct for the plane of interest, e.g., the endothelium. In this instance, the virtual image will be either anterior or posterior to the center of rotation and will, therefore, move laterally when the eye rotates. If the motion of the image is sufficiently small that it does not interfere with observation and diagnosis, the contact lens can be utilized. If the motion of the image is excessive, contact lenses of different powers may be substituted. The direction of motion determines whether a more positive or negative lens is needed. If the image moves in the same direction as the cornea moves, the image is located in front of the center of rotation and a more positive lens is needed while image movement in the opposite direction indicates a more negative lens.

Figure 5:
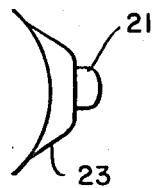
FIG. 5A illustrates an alternative contact lens.
FIG. 5B is a front view of the lens of FIG. 5A.
Figure 5:
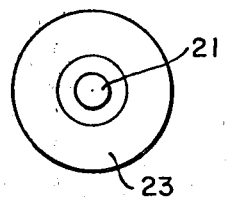

FIGS. 5a and 5b illustrate one alternative embodiment of the contact lens in which the optical element 21 and the contact element 23 are optically cemented or bonded together. The optical element 21 may be formed of PMMA, glass, or other optical quality material, and the posterior surface is polished flat so as to fit against the flat surface of element 23. The contact element 23 is made of a material such as PMMA, HEMA, CAB, silicone, or other similar material used in the fabrication of contact lenses.

Figure 6:
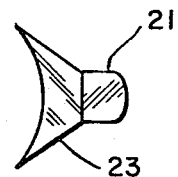
FIG. 6 illustrates another alternative contact lens.

In yet another alternative embodiment of the invention, the optical power may be distributed so as to gain aberration correction or a telephoto effect. As shown in FIG. 6, the posterior surface of the optical portion can be made spherical rather than flat, thus offering the possibility of aberration correction. Further combinations of lens elements and surfaces will be apparent to those skilled in the art of lens design.

Figure 7:
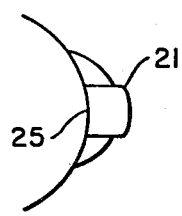
FIG. 7 illustrates another alternative contact lens construction.

A further variation is illustrated in FIG. 7, in which the optical element 21 extends through the contact element, so that the optical element makes contact with the cornea at surface 25. If the surface 25 is polished flat, it will have the effect of applanating the surface of the cornea in the region to be examined. This has the advantage that a larger region of the endothelium is in focus than if the cornea had its natural curvature.

Figure 8:
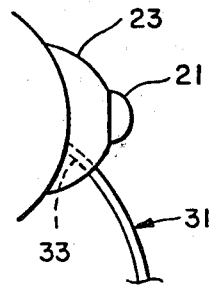
FIG. 8 illustrates a contact lens adapted to be used in conjunction with a vacuum suction means.

In order to better assure that the lens is held securely onto the eye, FIG. 8 illustrates an embodiment in which such security may be achieved. As seen in FIG. 8, a suction tube 31 connects to a passage 33 in the lens which leads to the cornea. By connecting the suction tube to a suction force, the lens 23 is securely held onto the eye.

Figure 9:
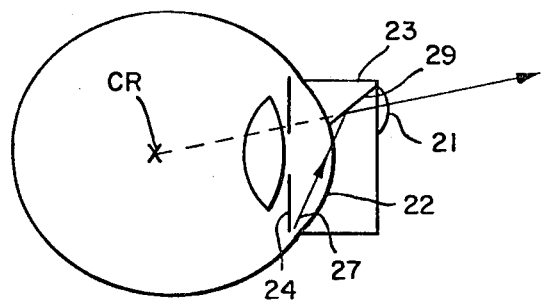
FIG. 9 illustrates another embodiment of the contact lens, adapted for viewing the angle of the anterior chamber of the eye.

In FIG. 9 the contact lens incorporates a mirror surface 29 which pemits viewing the anterior chamber in the vicinity of the so-called "angle," 27, where the cornea 22 and the iris 24 join. This type of mirror is well known in the art, being used in the Goldmann and other diagnostic contact lenses. In this case, a positive lens surface 21 is added to the anterior surface of the contact lens, the power of the surface being such as to form the virtual image of the angle at the center of rotation of the eye. In addition, the angle of the mirror surface 29 must be appropriate to permit the virtual image to be formed at the center of rotation and the contact lens must be adapted to move with the eye as the eye undergoes small, rapid rotational motions.

Figure 10:
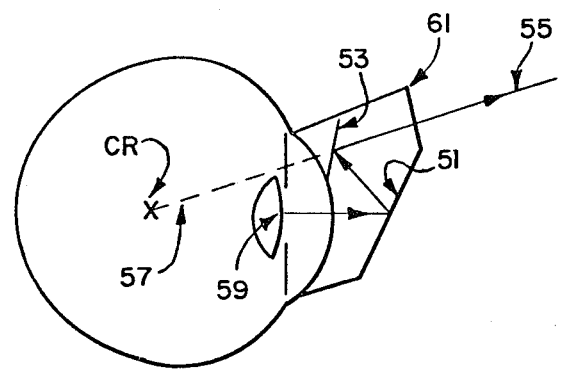
FIG. 10 illustrates the use of plane mirrors to form a virtual image of a region within the eye lens at the center of rotation of the eye.

FIG. 10 shows the use of two plane mirrors incorporated in the contact lens and positioned such that the virtual image of a point within the eye lens is located at the center of rotation of the eye. Reflecting surfaces 51 and 53 form a virtual image of point 59 at the center of rotation, CR, of the eye. Reflecting surface 53 is shown as being incorporated in the body of the contact lens 61.

Ray 55 indicates the actual path of the light from point 59 toward an observer, and dashed line 57 indicates the apparent path of the ray as seen by the observer. The distance between mirrors 51 and 53, and their angular orientation are selected so that the virtual image of point 59 is located at the center of rotation. By selecting a different spacing between mirror surfaces 51 and 53, the contact lens can be designed to form a virtual image of another point within the eye, e.g. the endothelial cell layer, at the center of rotation. It will be apparent to those skilled in the art that other combinations of plane mirrors, curved mirrors, and refracting elements can be designed to accomplish the same purpose.

Figure 11:
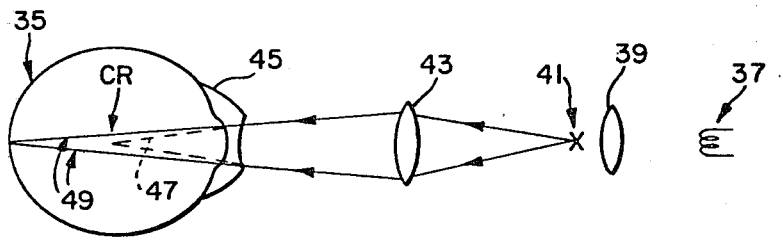
FIG. 11 illustrates the use of a contact lens together with an instrument to form a stabilized image on the retina.

FIG. 11 illustrates a different application for the image stabilizing contact lens. In this case the eye shown at 35 is that of the observer. An image of target 41 is projected to his retina by the system consisting of light source 37, lenses 39 and 43, and contact lens 45. The stationary instrument consisting of light source 37, target 41, and lenses 39 and 43 projects an image of the target 41 to the center of rotation of the eye, as indicated by the dashed lines 47. The function of the contact lens 45 is to alter the focusing action, so that together with the refractive elements of the eye, the image of the target is actually formed on the retina, as indicated by the solid lines 49.

The purpose of the arrangement of FIG. 11 is to form a stabilized image of a target on the retina of an observer, independent of small involuntary eye motions. It is known that such stabilized images have the interesting property that after a few seconds they appear to fade and then disappear entirely. Future application could include tests of visual fields in which fixation of the patient's visual axis would not be so great a problem as it is with present instruments.

For diagnostic examination of the eye, the invention as depicted in FIGS. 1 through 10 offers several important advantages. By reducing lateral image motion due to eye rotation, detailed examination of the eye structures is greatly facilitated. Furthermore, for studies of the endothelium, and other planes within the cornea or within the anterior chamber and lens, the focus becomes less critical than when using direct examination.

Yet another advantage of the invention is that by virtue of reducing image jitter, it is possible to examine eye tissues under higher magnifications than might conventionally be possible.

DESIGN PARAMETERS

In selecting the appropriate contact lens for purposes of the invention the first parameter to be established is the region of the interior of the eye which is to be visualized and stabilized. The next step is to determine the apparent position of the region or plane of interest, measured from the apex of the cornea. This is best expressed as the vergence, $V_1$, of the light from the plane of interest as it is incident on the interface between the cornea and the contact lens. The contact lens is then designed so that the virtual image of the region of interest is formed at the center of rotation of the eye. The design parameters are the thickness, t, of the contact lens, the index of refraction n of the contact lens, the distance s from the center of rotation to the cornea apex which is taken to be about 13.5 mm, and the radius, $r_2$, of the anterior surface. The radius of the posterior surface, $r_1$ must match that of the cornea which is generally about 7.8 millimeters.

In the case of the endothelium, the vergence $V_1$ may be simply calculated as follows. For light from an object at a distance x to the left of a refracting surface, the vergence of the light at the refracting surface is $-(n/x)$, where n is the index of the medium and x is in meters. For the cornea endothelium, x is the thickness of the cornea which is about 0.0005 meters and n is the index of the cornea, $n = 1.376$. Therefore $V_1 = -(1.376/0.0005) = -2752$.

To examine other points within the eye, calculation of the vergence $V_1$ is somewhat more involved because of the refractive power of the aqueous, the lens, and even the finite thickness of the cornea. An exact calculation of vergence $V_1$ can be carried out if the optical properties of the media between the plane of interest and the cornea are known. While these values are known for the average eye, anatomical differences between individuals would make a precise calculation for a particular patient impractical if not impossible. Therefore, it will be desirable to have available a selection of contact lenses each designed for a specific vergence value.

Equation (3) may obviously be satisfied by an infinite number of combinations of radius $r_2$ and thickness t. However, for practical reasons the thickness should not be greater than about 10 mm. nor thinner than perhaps 0.25 millimeters. Similarly, the practical range for radius $r_2$, should be from about 2 millimeters to infinity, although using special techniques, spherical lenses with radii smaller than 2 millimeters can be fabricated.

For purposes of illustration, the following are examples of $V_1$, t, and $r_2$ for several regions within the eye:

| Region | Vergence $V_1$ | $r_1$ | t | $r_2$ |
|---|---|---|---|---|
| Epithelium | infinity | 7.8 | 5 mm | 2.01 mm |
| Endothelium | 2752 D | " | 5 | 2.28 |
| Lens | | | | |
| anterior | 382 | " | 5 | 4.22 |
| central | 250 | " | 5 | 5.69 |
| posterior | 188 | " | 5 | 7.36 |
| Retina | | | | |
| emmotrope | 43 | " | 1 | −36.3 |
| −2D myope | 41 | " | 1.70 | −36.3 |
| −4D myope | 39 | " | 2.42 | −36.3 |
| +2D hyperope | 45 | " | 0.32 | −36.3 |

In the first five examples in the table, the thickness is kept constant at 5 millimeters and the required radius $r_2$ is calculated for each case. In the last four examples relating to contact lenses for retinal image stabilization, a constant radius $r_2$ was chosen and the required thickness was calculated for each case. The latter approach leads to economies of manufacture. In the case of endothelium and lens studies, it is not practical to maintain a constant radius $r_2$ for all values of vergence.

Although the invention has been described with respect to particular materials, sizes and shapes, it is to be understood that the invention is not limited to the particular embodiments disclosed but extends to all alternative embodiments falling within the scope of the claims.

What is claimed is:

1. A method of reducing the effects of rotational motion or jitter of an object while examining a region or plane within or on the object, said method comprising forming a virtual image of the region or plane of interest as the center of rotation of the object, thereby causing the virtual image to remain stabilized during examination despite rotation or jitter, and viewing said virtual image as part of said examination of said region or plane.

2. The method as defined by claim 1 comprising viewing said region or plane with a scanning microscope apparatus.

3. The method as defined by claim 1 wherein said object is an eye.

4. The method as defined by claim 3 comprising viewing said region or plane through a lens adapted to form said virtual image of said region or plane at said center of rotation.

5. The method as defined by claim 4 comprising viewing said region or plane through a contact lens affixed to said eye so as to move therewith.

6. The method as defined by claim 5 wherein said contact lens comprises a magnifying element.

7. The method as defined by claim 6 wherein a tube extends within said lens and said method comprises exerting a vacuum on said tube whereby said contact lens is securely held on said eye.

8. An optical system for viewing a region or plane within or on a rotating object, said optical system being adapted to move precisely with the object, and whereby said optical system is adapted to provide a virtual image of said region or plane at the center of rotation of the object, in order to reduce the effects of rotational motion or jitter on the image of said region or plane.

9. The optical system as defined by claim 8 which is adapted to fit on the cornea of the eye as a contact lens and is adapted to move with the eye as the eye undergoes rotational motions.

10. The optical system as defined by claim 9 wherein said contact lens has a radius of curvature of the anterior surface defined by the equation:

$$r_2 = \frac{(n - 1)(s + t)[t(r_1 V_1 - n + 1.376) - nr_1]}{[ns + t(n - 1)][r_1 V_1 - n + 1.376] + nr_1}$$

where:
$r_1$ = radius of curvature of the posterior surface of the contact lens
n = index of refraction of the contact lens
s = distance from the center of rotation to the cornea apex, taken to be 13.5 mm
t = center thickness of the contact lens
$V_1$ = vergence of the light from the plane or region as it is incident on the interface between the cornea and the contact lens.

11. The optical system as defined by claim 9 comprising an optical element fitted within a bore provided in said contact lens.

12. The optical system as defined by claim 9 wherein said contact lens is adapted to form a virtual image of the endothelial cell layer at or near the center of rotation of the eye.

13. The optical system as defined by claim 9 wherein said contact lens is adapted to form a virtual image of a region within the cornea at or near the center of rotation of the eye.

14. The optical system as defined by claim 9 wherein said contact lens is adapted to form a virtual image of a region within the eye lens at or near the center of rotation of the eye.

15. The optical system as defined by claim 9 wherein said contact lens is adapted to form at the center of rotation of the eye a virtual image of a region within the vitreous near the lens or a region within the vitreous near the retina.

16. The optical system as defined by claim 9 wherein said contact lens is adapted to form a virtual image of a portion of the retina at the center of rotation of the eye.

17. The optical system as defined by claim 9 wherein said contact lens is adapted to form a virtual image of the angle of the anterior chamber at the center of rotation of the eye.

18. The optical system as defined by claim 9 including a tube extending within said lens adapted to contact the outer surface of said eye being examined.

19. The optical system as defined by claim 9 wherein said lens comprises a contact portion and an optical portion bonded thereto.

20. The optical system as defined by claim 9 further comprising two reflecting surfaces positioned to form a virtual image of said plane or region within the eye at the center of rotation of the eye.

21. Image stabilization apparatus comprising:
(a) an optical instrument for viewing a region or plane on or in an object which rotates or jitters around a center of rotation; and
(b) means for creating a virtual image of said region or plane substantially at said center of rotation of the object, to minimize the effects of jitter and rotation as said plane or region is viewed through said instrument.

22. The apparatus as defined by claim 21 wherein said means comprises a lens attached to said object and through which said plane or region is viewed.

23. The apparatus as defined claim 22 wherein said lens is a contact lens adapted to be placed directly on said object.

24. The apparatus as defined by claim 23 wherein said contact lens comprises a lens element fitted within a bore provided in said lens.

25. The apparatus as defined by claim 23 wherein a tube extends within said lens and is adapted to extend to contact the outer surface of the object being examined.

26. The apparatus as defined by claim 23 wherein said contact lens comprises a contact portion and an optical portion bonded thereto.

27. The apparatus as defined by claim 23 wherein said optical instrument is a microscope.

28. The apparatus as defined by claim 21 wherein said optical instrument is adapted to photograph said region or plane.

29. The apparatus as defined by claim 21 wherein said means comprises one or more mirrors attached to said object and which serve to reflect light from said region or plane to said optical instrument.

30. The optical system as defined by claim 10 wherein said contact lens has an outer convex surface having a radius of 7.36 mm or less.

31. The optical system as defined by claim 10 wherein said contact lens has a concave outer surface having a radius of −36.3 mm or less.

* * * * *